United States Patent [19]
Beran et al.

[11] Patent Number: 5,785,723
[45] Date of Patent: Jul. 28, 1998

[54] POSITIVE PRESSURE FILTER SYSTEM FOR INFLATABLE BLANKET HEATERS

[75] Inventors: Anthony V. Beran, Santa Ana; Gordon Y. Shigezawa, Irvine, both of Calif.

[73] Assignee: Respiratory Support Products, Irvine, Calif.

[21] Appl. No.: 546,678

[22] Filed: Oct. 23, 1995

[51] Int. Cl.$^6$ .................................................. B01D 46/12
[52] U.S. Cl. ........................ 55/267; 55/356; 55/385.1; 55/472; 55/487; 55/494; 55/502; 607/104; 607/108
[58] Field of Search .................. 55/502, 472, 494, 55/503, 508, DIG. 28, 267, 385.1, 356, 471, 473, 482, 487; 210/321.78, 321.8; 607/96, 104, 108

[56] References Cited

U.S. PATENT DOCUMENTS

| | | | |
|---|---|---|---|
| 4,440,555 | 4/1984 | Chichester | 55/DIG. 28 |
| 4,488,889 | 12/1984 | McCarroll | 55/502 |
| 4,810,269 | 3/1989 | Stackhouse et al. | 55/267 |
| 5,066,318 | 11/1991 | McDonough | 55/502 |
| 5,129,928 | 7/1992 | Chan et al. | 55/267 |
| 5,182,019 | 1/1993 | Cote et al. | 210/321.8 |
| 5,222,488 | 6/1993 | Forsgren | 55/502 |
| 5,300,098 | 4/1994 | Philipot | 607/96 |
| 5,366,625 | 11/1994 | Pedersen et al. | 210/321.78 |
| 5,417,729 | 5/1995 | Greenleaf, Sr. | 55/502 |

OTHER PUBLICATIONS

Brochure for Bair Hugger Cub Blanket, Augustine Medical, Inc. 1993.
Brochure for Blair Hugger Chest Access Blanket, Augustine Medical, Inc., 1992.
Brochure for Bair Hugger Torso Blanket Model 530, Augustine Medical, Inc., Jan. 1, 1993.
Brochure for Bair Hugger Multi-Access Blanket, Augustine Medical, Inc. 1992.
Brochure and Operations Manual for Bair Hugger Warming System, Model 200, Augustine Medical, Inc., 1993.
Brochure for Advanced Bair Hugger Patient Warming System, Augustine Medical, Inc., 1993.
Brochure for 241 Fluid Warming, Augustine Medical, Inc., 1994.
Brochure for Thermacare Patient Comfort System, Gaymar Industries, Inc., 1992.
Brochure for The Warm Air Warming Tube, Bimeco, May 1993.

*Primary Examiner*—C. Scott Bushey
*Attorney, Agent, or Firm*—Price, Gess & Ubell

[57] ABSTRACT

An inflatable blanket heater draws room air into the unit through a filtered intake by an electrically-powered blower. The air is compressed by the blower and warmed by an electric heater in the unit. The warmed air is forced through an outlet filter that removes air particles down to 0.2-micron. The filtered warmed air is delivered to a convective (inflatable) heating blanket by an air delivery hose.

17 Claims, 2 Drawing Sheets

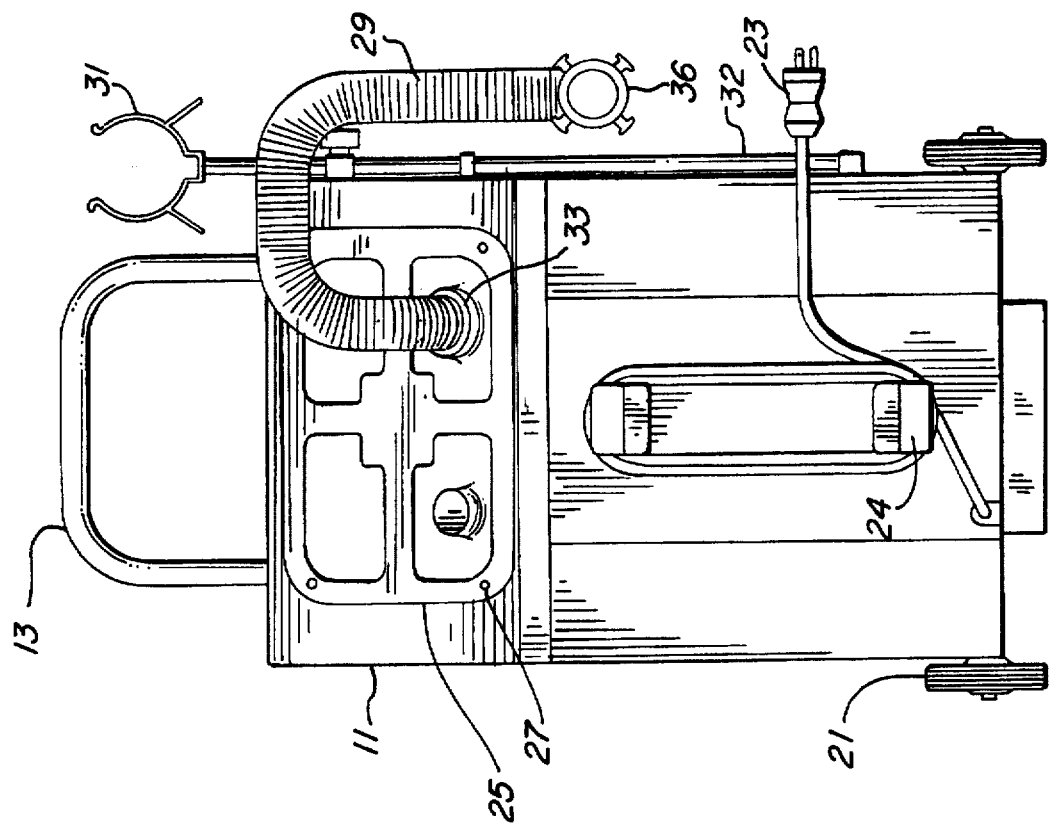
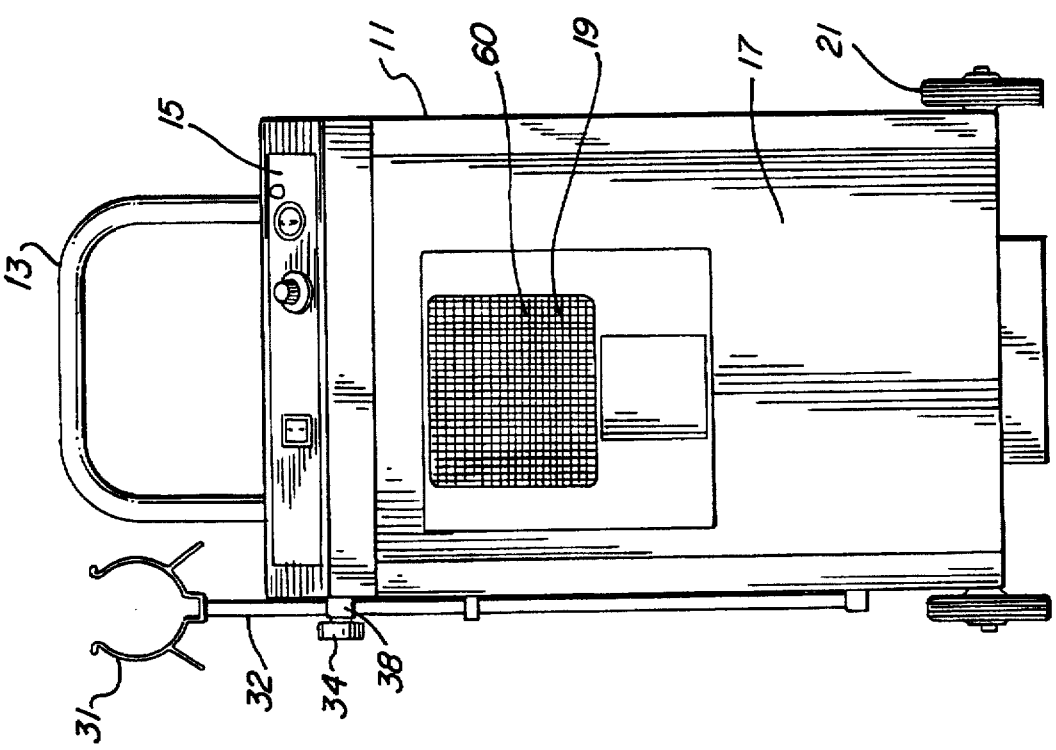

POSITIVE PRESSURE FILTER SYSTEM FOR INFLATABLE BLANKET HEATERS

BACKGROUND OF THE INVENTION

1. Field of the Invention

The present invention relates generally to improvements in air filters and, more particularly, pertains to a new and improved air filtration system used in heater units for supplying air to inflatable blankets which are used to maintain a certain body temperature for hospital patients, for example.

2. Description of Related Art

In the field of inflatable blanket heaters, it has been a practice to employ an electrically-powered blower and an electric heater to heat the air being supplied to the inflatable blanket which is, in turn, distributing the warmed air over the body of a patient. The temperature of the heated air can be controlled through the electric heater. Traditionally such units draw in ambient air which is heated and then distributed to the surface areas of the patient. This ambient air is typically filtered at the intake. Although filters are utilized in these units for the ambient air drawn from a hospital environment, these filters have been unsatisfactory, particularly in situations where the air is being used to warm the body of a patient that is highly susceptible to infection through the skin, such as a burn patient, for example, or by inadvertent airflow over a surgical field. Hospitals are known for having environments that contain many impurities. The impurities of concern are generated outside of the inflatable blanket heater, as well as, perhaps, by the blower and heater units themselves.

OBJECTS AND SUMMARY OF THE INVENTION

An object of the present invention is the provision of an inflatable blanket heater that is highly efficient.

Another object is to provide a filter system for an inflatable blanket heater that filters out particles as small as 0.2-micron.

These objects and the general purpose of this invention are accomplished by utilizing a filter at an outlet of the inflatable blanket heater which filter is constructed to provide highly efficient particulate removal. The filter has a body with an input and an output aperture. A filter media that filters out up to 0.2-micron particles is sealed by its perimeter edges to the interior of the filter. A lid with an outlet port is sealed to the output aperture of the filter body. Filtering air at the output with the positive outlet pressure prevents drawing particles through inescapable leaks in the air delivery system, assuring delivery of clean air.

BRIEF DESCRIPTION OF THE DRAWINGS

Other objects and many of the features and advantages of the invention will be readily appreciated as the invention becomes better understood upon reading the following detailed description in conjunction with the accompanying drawings, in which like reference numerals designate like parts throughout the figures thereof, and wherein:

FIG. 1 is a front elevation of a preferred embodiment of the inflatable blanket heater;

FIG. 2 is a rear elevation of the unit shown in FIG. 1;

DETAILED DESCRIPTION OF THE PREFERRED EMBODIMENTS

Figure 4:
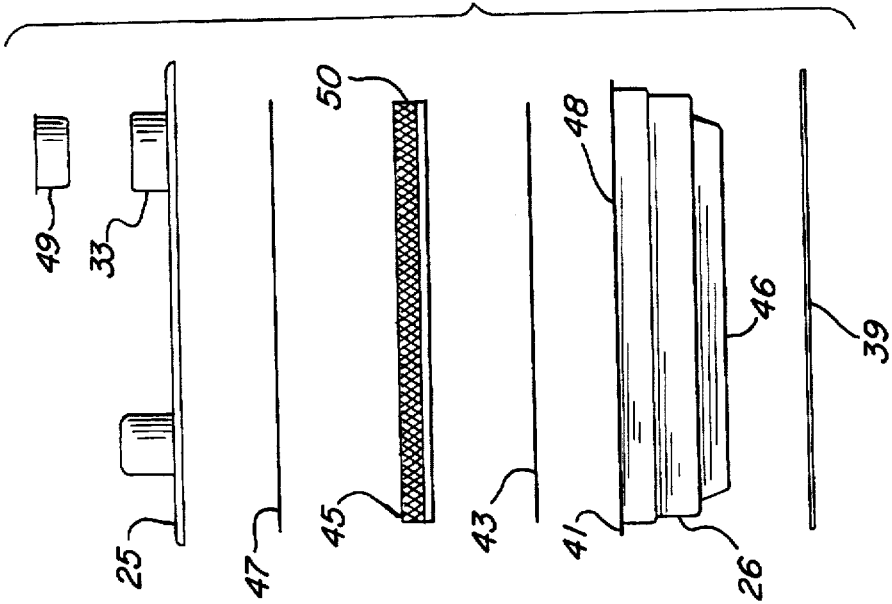
FIG. 4 is an exploded view of the filter assembly shown as a single unit in FIG. 3.

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide assurance of delivery of filtered air of known particle size limit to site of patient application.

FIG. 1, which illustrates the entire inflatable blanket heater unit within which the filter system of the present invention is located in its preferred embodiment, shows the inflatable blanket heater as comprising a cabinet 11 mounted on wheels 21 with a curved handle 13 attached to the cabinet 11. The front panel 17 of cabinet 11 contains an air intake opening 19 which may contain an intake filter 60 therein. The heater unit, in addition, has a control panel 15 for setting the air temperature desired. A hose support bracket 31 is mounted on a shaft 32 which slides within a sleeve block 38. The block 38 has a hand-operable bolt 34 threaded therein to hold fast rod 32 at selected positions.

FIG. 2 illustrates the back side of the inflatable blanket heater of FIG. 1, showing the power cord 23 going into cabinet 11 with storage brackets 24 mounted thereon. The power cord 23 is shown wound around the storage brackets 24.

An outlet filter lid 25 is mounted to the cabinet 11 by at least four mounting screws 27. Lid 25 has an outlet port 33 to which is attached a warm air conducting hose 29. Hose support bracket 31 aids in positioning hose 29. At the other end of hose 29, an attachment mechanism 36 is utilized for attaching the hose to any number of patient-warming blankets, such as manufactured by the inventors herein or the BAIR HUGGER manufactured by Augustine Medical, the WARM TOUCH manufactured by Mallinckrodt Medical, and the THERMOCARE manufactured by Gamar, for example.

Figure 3:
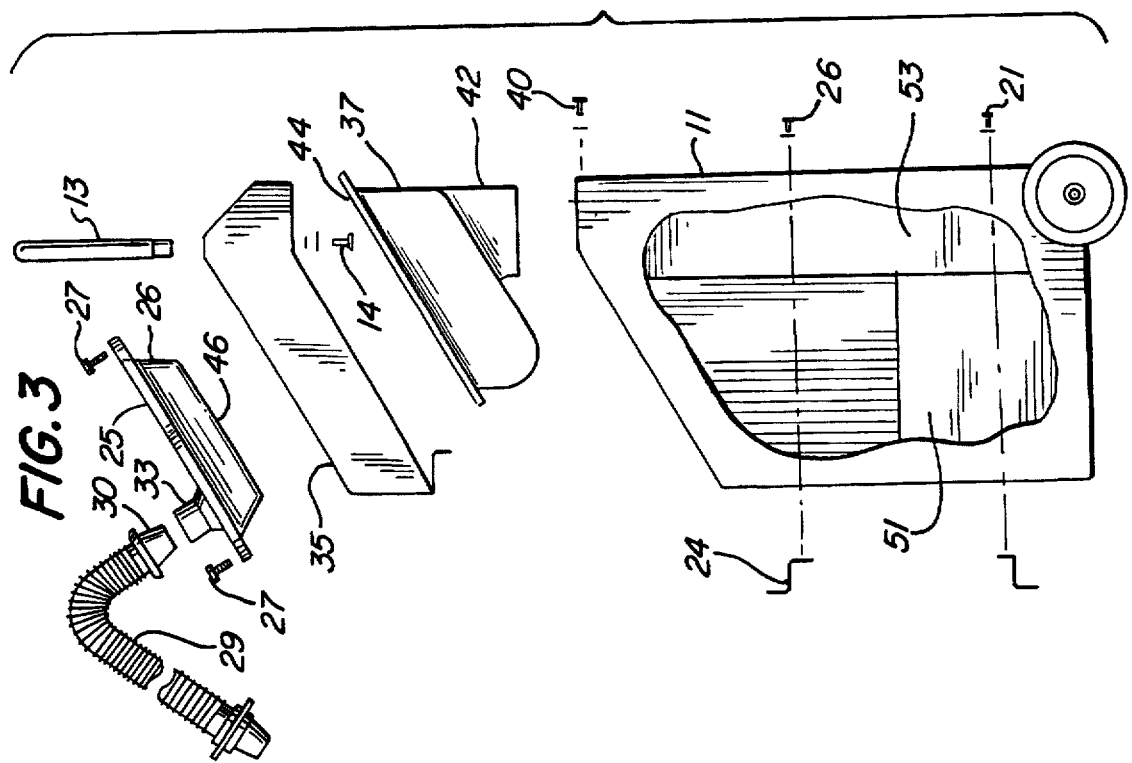
FIG. 3 is a partially exploded side elevation of the unit shown in FIG. 1 with a portion thereof broken away.

FIG. 3 illustrates, in an exploded manner and in cutaway, various features of the preferred embodiment of the present invention in more detail. The cabinet 11 is shown in side view with a cutaway illustrating the electrically-powered blower 51 and a heating column 53. The heating column 53 may be a plenum chamber containing an electric heater used to heat the air within. Plenum chamber 53 has an outlet port (not shown) which mates with a lower inlet port extension 42 of a filter bin 37. Filter bin 37, in assembly, resides completely within cabinet 11. Overlaying filter bin 37 is the cabinet top 35 to which is fastened the handlebar 13 by way of bolts 14.

The cabinet top 35 has an aperture therein which allows the outlet filter body 26 with the lid 25 attached thereto to seal to the perimeter of the upper rim 44 of bin 37, the filter body 26 resting within bin 37 in assembly. Outlet filter body 26 has an open bottom 46. Lid 25 has an air outlet port 33 to which a mating couple 30 from an air transport hose 29 attaches.

Referring now to FIG. 4, which illustrates an exploded view of the outlet filter assembly of FIG. 3 with the lid 25 on top and the outlet filter body 26 on the bottom, the entire outlet filter assembly is fastened to the cabinet top 35 (FIG. 3) and sealed against cabinet top 35 by a gasket 39 being compressed between the underside of lid 25 and cabinet top 35 by the filter mounting screws 27.

Filter media 45 is sandwiched between an apertured upper potting plate 47 and a lower potting plate 43, which is cemented to and forms a part of filter media 45. The filter media assembly is then placed into the outlet filter body 26, which has an open bottom 46 and an open top 48. The filter body 26 has a stepped configuration, as shown in FIG. 4. The perimeter edge 50 of the filter media 45, with the potting plates 47 and 43, is sealed to the internal walls of the outlet filter body, preferably by a urethane potting compound. The middle of the filter is left clear to pass airflow entering at the open bottom 46 of the filter body, through the filter media 45 and out the open top 45 of the filter body to the lid 25, and out an exit port 33. The lid 25 caps the outlet filter body 26 and is sealed to the lip 41 of filter body 26, preferably by an ABS cement.

In operation, the inflatable blanket heater takes in ambient air through the air intake opening 19 in the cabinet 11 and inlet filter 60 as a result of blower 51 drawing in ambient air and compressing it in plenum chamber 53 containing electrical heater elements which warm the air and pass it to the intake extension 42 of filter bin 37. The top 44 of outlet filter bin 37 is sealed by cabinet top 35 and filter body lid 25, thus forcing the air through the bottom opening 46 of filter body 26. The warmed air passes through filter media 45 located within filter body 26 to output port 33 in the lid 25.

During transport, the outlet port 33 in lid 25 is capped temporarily by cap 49.

The filter media 45 is preferably a material of the kind that has the capability of removing from the warm air passing through it, particulate matter that is as small as 0.2-micron. Placement of the 0.2-micron filter at the outlet side of the heater, rather than at the inlet side before the blower, assures that air passing through the filter is under positive pressure relative to ambient. Any minute leak following or before the filter will not serve as a path for particulate entry to the airstream. In contrast, filtering at the inlet requires a system which has no leaks in the airflow path up to the blower, including flow through the filter and cabinet. The resulting airflow delivered by Applicants' embodiment is contaminate-free and a major improvement over the inflatable blanket heaters of the prior art.

It should be understood, of course, that the foregoing disclosure relates only to a preferred embodiment of the invention, and that modifications may be made therein without departing from the spirit and scope of the invention as set forth in the appended claims.

What is claimed is:

1. In combination with an inflatable blanket heater having a cabinet housing, an air blower, and an air heater, said cabinet having an air intake opening and an air outlet opening therein, an improved air filter system, comprising:
   a filter bin located in said cabinet at the air outlet opening, said filter bin having an air inlet aperture and an air outlet aperture;
   a cabinet top fastened to the cabinet and to said filter bin having an aperture therein around said filter bin outlet aperture;
   a filter body having an open top and open bottom located in said filter bin and sealed to the perimeter of the bin;
   a filter media having a top and bottom located within the filter body with a perimeter of said filter media sealed to the interior of the filter body; and
   a lid having an outlet port, said lid sealed to a portion of the top of the filter body to enable air to flow into the air intake opening of said cabinet to be pressurized by the air blower above ambient pressure, heated by the heater located therein, and continue to flow out the air outlet opening into the air inlet of said filter bin, into the open bottom of said filter body, through the filter body, and out the outlet port of said lid.

2. The improved filter system of claim 1 wherein said filter media comprises filter material that removes airborne particles down to 0.2-micron in diameter.

3. The improved filter system of claim 1 further comprising:
   an apertured lower potting plate located within said filter body to which a portion of the bottom of said filter media is sealed; and
   an apertured upper potting plate located within said filter body to which a portion of the top of said filter media is sealed.

4. The improved filter system of claim 1 wherein said filter body comprises a bottom opening that is smaller than the top opening.

5. The improved filter system of claim 1 wherein the outlet port on said lid is smaller than the top opening of the filter body.

6. The improved filter system of claim 1 further comprising a hose coupling located at the outlet port on said lid.

7. The improved filter system of claim 1 further comprising a gasket for sealing the perimeter of said filter body to the outlet of said heater.

8. The improved filter system of claim 1 wherein the filter bin air inlet aperture is sealed to the output of the air heater.

9. The improved filter system of claim 1 wherein said cabinet top has its aperture sealed to outlet aperture of said filter bin.

10. The improved filter system of claim 1 wherein said filter body is sealed to the perimeter of said filter bin by a sealing gasket.

11. The improved filter system of claim 1 wherein said lid is sealed to the perimeter of the top of said filter body.

12. An inflatable blanket heater air filter system comprising:
   a cabinet housing having an air intake opening;
   an intake air filter mounted in the air intake opening;
   an air blower mounted in the cabinet housing to draw air through the air intake filter;
   an air heater mounted in the cabinet housing to heat the air in the cabinet housing;
   a filter bin located in the cabinet housing at a heated air outlet opening in the cabinet housing;
   an exhaust air filter cartridge mounted in the air outlet opening in the cabinet housing, including a cartridge filter body having a stepped configuration, an apertured upper potting plate, an apertured lower potting plate, a filter media sandwiched between the upper and lower potting plates and positioned in the stepped configuration, a potting compound sealing the respective perimeters of the upper and lower potting plates and filter media to the cartridge filter body and a lid sealed to the cartridge filter body having an extended exit port member of a configuration to mount an air transport hose for connection to an inflatable blanket; and
   a cabinet lid sealed to the exhaust air filter cartridge and fastening the exhaust air filter cartridge in the heated air outlet opening, wherein replaceable exhaust air filter cartridges can be provided for use with patients and the heated air is pressurized by the air blower to an above ambient pressure.

13. The invention of claim 12 wherein the cartridge filter body is larger adjacent the cabinet lid and decreases in size towards the opposite end.

14. The invention of claim 13 wherein the filter media consists of filter material that removes airborne particles to 0.2 microns in diameter.

15. The invention of claim 14 wherein the cabinet lid has four apertures with the extended exit port member extending through one of the apertures.

16. The invention of claim 15 wherein the intake air filter is mounted in the air intake opening on a side of the cabinet housing and the exhaust air filter cartridge is mounted on a top of the cabinet housing.

17. An inflatable blanket heater air filter system, comprising:

a portable operator-driven cabinet housing having side walls and a top wall, one of the side walls includes an air intake opening;

an intake air filter mounted in the air intake opening of the side wall;

an air blower mounted in the cabinet housing to draw air through the air intake filter;

an air heater mounted in the cabinet housing to heat the air in the cabinet housing;

a filter bin located in the cabinet housing at a heated air outlet opening in the top wall of the cabinet housing;

an exhaust air filter cartridge mounted in the air outlet opening in the cabinet housing, including a cartridge filter body having a stepped configuration, an apertured upper potting plate, an apertured lower potting plate, a filter media sandwiched between the upper and lower potting plates and positioned in the stepped configuration, the filter media includes filter material that removes airborne particles down to 0.2 micron in diameter, a potting compound sealing the respective perimeters of the upper and lower potting plates and filter media to an interior of the cartridge filter body and a filter lid sealed to the cartridge filter body having an extended exit port member of a configuration to mount an air transport hose over the exit port member for connection to an inflatable blanket;

means for sealing the exhaust air filter cartridge; and a removable cabinet lid sealed to the exhaust air filter cartridge by the sealing means and fastening the exhaust air filter cartridge in the heated air outlet opening, wherein replaceable exhaust air filter cartridges can be provided for use with patients and the heated air is pressurized by the air blower to an above ambient pressure.

* * * * *